United States Patent
Hauer et al.

(10) Patent No.: US 6,844,459 B2
(45) Date of Patent: Jan. 18, 2005

(54) PHARMACEUTICAL COMPOSITION

(75) Inventors: Birgit Hauer, Lahr (DE); Armin Meinzer, Freiburg-Munzingen (DE); Ulrich Posanski, Freiburg (DE); Jacky Vonderscher, Riedisheim (FR)

(73) Assignee: Novartis AG, Basel (CH)

( * ) Notice: Subject to any disclaimer, the term of this patent is extended or adjusted under 35 U.S.C. 154(b) by 219 days.

(21) Appl. No.: 10/441,406
(22) Filed: May 20, 2003

(65) Prior Publication Data
US 2003/0199433 A1 Oct. 23, 2003

Related U.S. Application Data

(63) Continuation of application No. 10/094,781, filed on Mar. 11, 2002, now abandoned, which is a continuation of application No. 09/871,858, filed on Jun. 1, 2001, now abandoned, which is a continuation of application No. 09/690,400, filed on Oct. 17, 2000, now Pat. No. 6,258,808, which is a continuation of application No. 09/488,215, filed on Jan. 19, 2000, now Pat. No. 6,262,022, which is a continuation of application No. 09/312,170, filed on May 14, 1999, now abandoned, which is a continuation of application No. 08/979,495, filed on Nov. 26, 1997, now abandoned, which is a continuation of application No. 08/490,600, filed on Jun. 6, 1995, now abandoned, which is a continuation of application No. 08/233,152, filed on Apr. 25, 1994, now abandoned, which is a continuation of application No. 07/906,208, filed on Jun. 25, 1992, now abandoned.

(30) Foreign Application Priority Data

Jun. 27, 1991 (GB) ............................................. 9113872

(51) Int. Cl.[7] ............................................. C07C 57/00
(52) U.S. Cl. ........................ 554/227; 554/224; 514/547
(58) Field of Search ............................... 554/224, 227; 514/547

(56) References Cited

U.S. PATENT DOCUMENTS

| | | | |
|---|---|---|---|
| 3,288,824 A | 11/1966 | Mahler et al. | 260/410.6 |
| 3,813,345 A | 5/1974 | Urton | 252/312 |
| 3,954,967 A | 5/1976 | Urton | 424/78 |
| 4,073,943 A | 2/1978 | Wretlind et al. | 424/358 |
| 4,146,499 A | 3/1979 | Rosano | 252/186 |
| 4,156,719 A | 5/1979 | Sezaki et al. | 424/177 |
| 4,388,307 A | 6/1983 | Cavanak | 424/177 |

(List continued on next page.)

FOREIGN PATENT DOCUMENTS

| | | |
|---|---|---|
| AT | 70043/87 | 10/1987 |
| BE | 895724 | 7/1983 |
| CA | 1209361 | 8/1986 |
| CH | 2 461 786 | 6/1983 |
| CH | 8634788 | 6/1983 |
| CH | 641356 | 2/1984 |
| DE | 3315805 | 11/1984 |
| EP | 274431 | 7/1983 |
| EP | 135171 | 3/1985 |
| EP | 170623 | 2/1986 |
| EP | 211 258 | 2/1987 |

(List continued on next page.)

OTHER PUBLICATIONS

95:225610K, Anon. (1981).
Anon., Research Disclosure 21143 (Nov. 1981).
Beyer et al., Pharmazie in unserer Zeit, Vol. 12(2):55–60 (1983).
Bhargava et al., Pharmaceutical Technology, Mar. 1987.
Carrigan et al., J. Pharm. Sci., Vol. 62, pp. 1476–1479 (1973).

(List continued on next page.)

Primary Examiner—Deborah D. Carr
(74) Attorney, Agent, or Firm—Gabriel Lopez

(57) ABSTRACT

Pharmaceutical compositions comprising a cyclosporin in a novel galenic formulations for oral administration. The compositions typically comprise a cyclosporin, 1,2-propylene glycol, a mixed mono-, di- and tri-glyceride and a hydrophilic surfactant. Further a refined glycerol-transesterified corn oil is provided representing a mixed mono-, di- and tri-glyceride suitable for the novel formulation. Dosage forms include in particular oral dosage forms.

20 Claims, 3 Drawing Sheets

U.S. PATENT DOCUMENTS

| | | | |
|---|---|---|---|
| 4,482,576 A | 11/1984 | Boot et al. | 426/603 |
| 4,567,161 A | 1/1986 | Posanski et al. | 424/199 |
| 4,652,406 A | 3/1987 | Lepper et al. | 260/410.9 |
| 4,695,450 A | 9/1987 | Bauer et al. | 424/168 |
| 4,719,239 A | 1/1988 | Muller et al. | 514/785 |
| 4,794,000 A | 12/1988 | Ecanow | 424/457 |
| 4,797,272 A | 1/1989 | Linn et al. | 424/59 |
| 4,797,273 A | 1/1989 | Linn et al. | 424/59 |
| 4,798,823 A | 1/1989 | Witzel | 514/11 |
| 4,835,002 A | 5/1989 | Wolf et al. | 426/590 |
| 4,888,239 A | 12/1989 | Brox | 428/402.2 |
| 4,914,188 A | 4/1990 | Dumont et al. | 530/317 |
| 4,963,367 A | 10/1990 | Ecanow | 424/484 |
| 4,990,337 A | 2/1991 | Kurihara et al. | 424/427 |
| 4,996,193 A | 2/1991 | Hewitt et al. | 514/11 |
| 5,037,653 A | 8/1991 | Dawson | 424/405 |
| 5,047,396 A | 9/1991 | Orban et al. | 424/405 |
| 5,154,754 A | 10/1992 | Damo et al. | 71/DIG. 1 |
| 5,206,219 A | 4/1993 | Desai | 514/3 |
| 5,338,761 A | 8/1994 | Nakajima et al. | 514/772 |
| 5,342,625 A | 8/1994 | Hauer et al. | 424/455 |
| 5,441,738 A * | 8/1995 | Klein et al. | 424/195.1 |
| 5,525,590 A | 6/1996 | Bollinger et al. | |
| 5,639,724 A | 6/1997 | Cavanak | 514/11 |
| 5,756,450 A | 5/1998 | Hahn et al. | 514/9 |

FOREIGN PATENT DOCUMENTS

| | | |
|---|---|---|
| EP | 256856 | 2/1988 |
| EP | 314689 | 5/1989 |
| EP | 0 315 079 | 5/1989 |
| EP | 0 361 928 | 4/1990 |
| EP | 0 378 893 | 7/1990 |
| FR | 2 553 661 | 4/1985 |
| FR | 2 642 650 | 8/1990 |
| GB | 616190 | 1/1949 |
| GB | 1171125 | 11/1969 |
| GB | 2 015 339 A | 9/1979 |
| GB | 2 098 865 | 12/1982 |
| GB | 2 206 119 | 12/1988 |
| GB | 2 209 671 | 5/1989 |
| GB | 2 211 408 | 7/1989 |
| GB | 2 211 848 | 7/1989 |
| GB | 2 218 334 | 11/1989 |
| GB | 2 221 157 A | 1/1990 |
| GB | 2222770 | 3/1990 |
| GB | 2 224 205 A | 8/1990 |
| GB | 2 228 198 A | 8/1990 |
| GB | 2 230 440 A | 10/1990 |
| JP | 280435 | 4/1985 |
| JP | 61/249918 | 11/1986 |
| WO | 8602264 | 4/1986 |
| WO | 87/01035 | 2/1987 |
| WO | 88/00059 | 1/1988 |
| WO | 90/08537 | 8/1990 |
| WO | 91/08676 | 9/1991 |
| WO | 93/09211 | 5/1993 |
| WO | 93/20833 | 10/1993 |

OTHER PUBLICATIONS

Cavanak and Sucker, Prog. Allergy vol. 38:65–72 (1986).
Charley, Helen, Food Science, 2nd edition, John Wiley & Sons (1982).
Derwent Abstract 1989–094742.
Derwent Abstract 1989–334771.
Derwent Abstract 1990–085699.
Derwent Abstract 84–069426/12.
Derwent Abstract 86–335072.
Derwent Abstract 87–024776.
Derwent Abstract 89–229298/32.
Derwent Abstract 90–255218/34.
Derwent Abstract 92–216793/26.
Derwent Abstract 92–235168/29.
Derwe et al., Br. J. Clin. Pharmac. vol. 33, pp. 39–43 (1992).
Ekman, S., Lipids 22:657–663 (1987).
Frazer et al., J. Physiol. vol. 103, pp. 306–310 (1994).
Hahn, Biodegradable Tensides (1988) (translation).
Jayakrishnan, et al., J. Soc. Cosmet, Chem. 34:335–350 (1983).
Mizushima, 86–335072/51 (Jul. 26, 1985).
Murbarak, Development and Testing of New Microemulsions (1982) (translation).
Muller, et al., Pharm. Ind. 50 (11): 1301–1306 (1988) (translation).
Muller, et al., Pharm. Ind. 50(3): 370–375 (1988) (translation).
Pohler, Micro–Emulsion Gels Structural Investigations and Galenical Properties (1983) (translation).
Remington's Pharmaceutical Sciences (17th ed.) Microemulsions, Chap. 20, pp. 298–299 (1985).
Reymond et al., Pharmaceutical Research vol. 15(10): 673–767 (1988).
Reymond, et al., Pharmaceutical Research vol. 5(10): 677–679 (1988).
Reymond, In Vitro In Vivi Model for the Absorption of Cyclosporin A (1986) (translation).
Ritschel, et al., Meth Find Exp Clin Pharmacol, vol. 12, pp. 127–134 (1990).
Ritschel, et al., Meth Find Exp Clin Pharmacol. vol. 11(4):281–287 (1989).
Ritschel, et al., Pharmaceutical Research vol. 5(10): Suppl. 108, PD 943 (1988).
Stupar et al., Goldschmidt Inforwist Essein. vol. 52: 22–28 (1982) translation.
Takada et al., Int. of Pharmaceutics, vol. 44:107–116 (1988).
Takada et al., J. Pharmaceutical REsearch vol. 3(1):48–51 (1986).
Takada et al., J. Pharmacobio–Dyn. vol. 11:80–87 (1988).
Takada et al., J. Pharmacobio–Dyn. vol. 8:320–323 (1985)Ziegenmeyer.
Takada et al., J. Pharmacobio–Dyn. vol. 9:156–160 (1986).
Takada, 87–024776/04 (Apr. 4, 1985).
Tarr et al., Pharmaceutical Research, vol. 6(1):40–43 (1989).
The Merck Index, 9th Edition, Merck & Co., Inc., Rahway, NJ, p. 1017 (1976).
Ulmans's Encyclopaedia of Industrial Pharmacy, vol. A9 (1987), pp. 298–299 and 308–311 (1987).
W. A. Ritschel, Meth Find Exp Clin Pharmacol, vol. 13(3) pp. 205–220 (1991).
Yanagawa et al., J. Microencapsulation 6(2): 161–164 (1989).
Ziegenmeyer, et al., Acta Pharmaceutical Technologica, vol. 26(4):273–275 (1980) (translation).

* cited by examiner

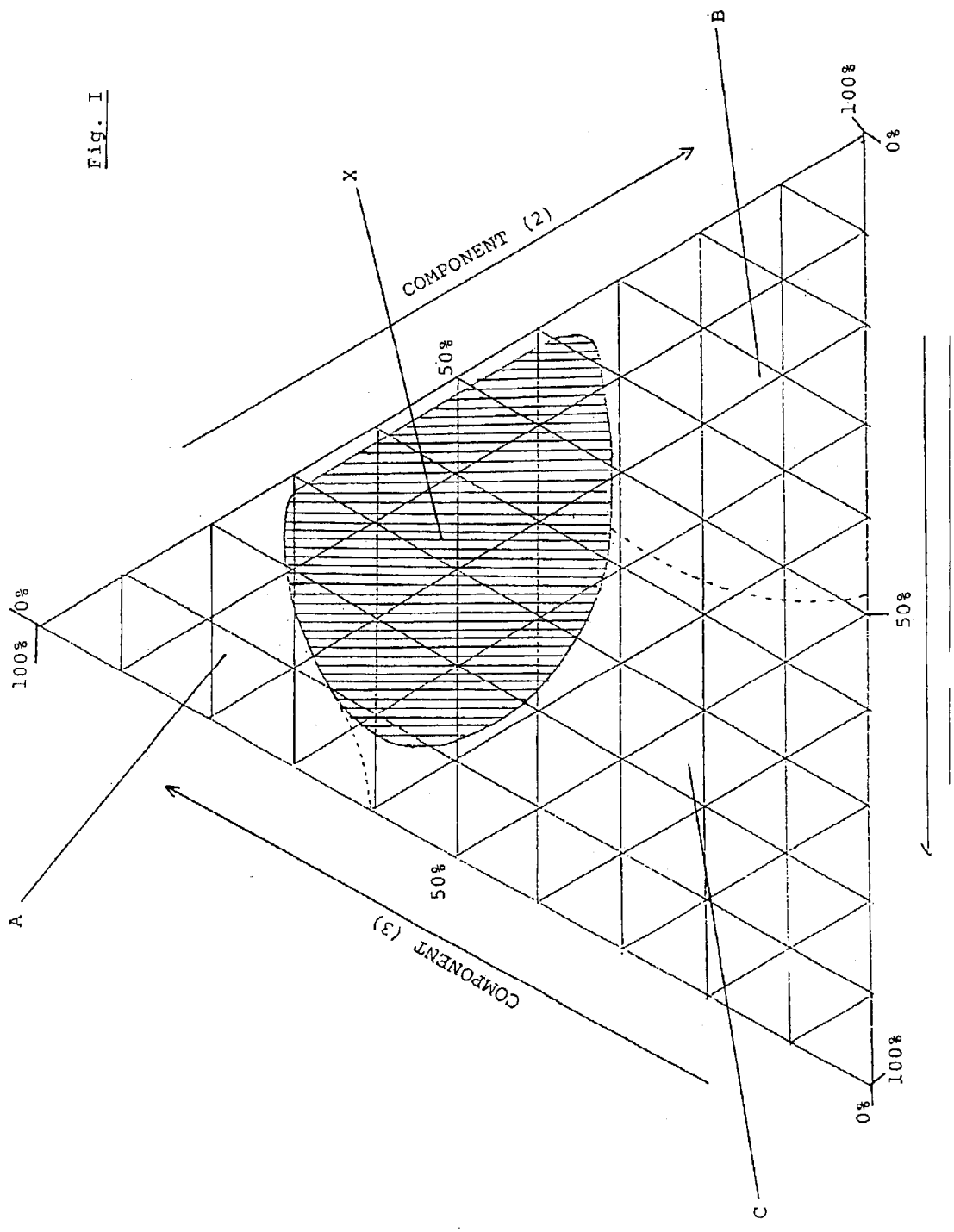

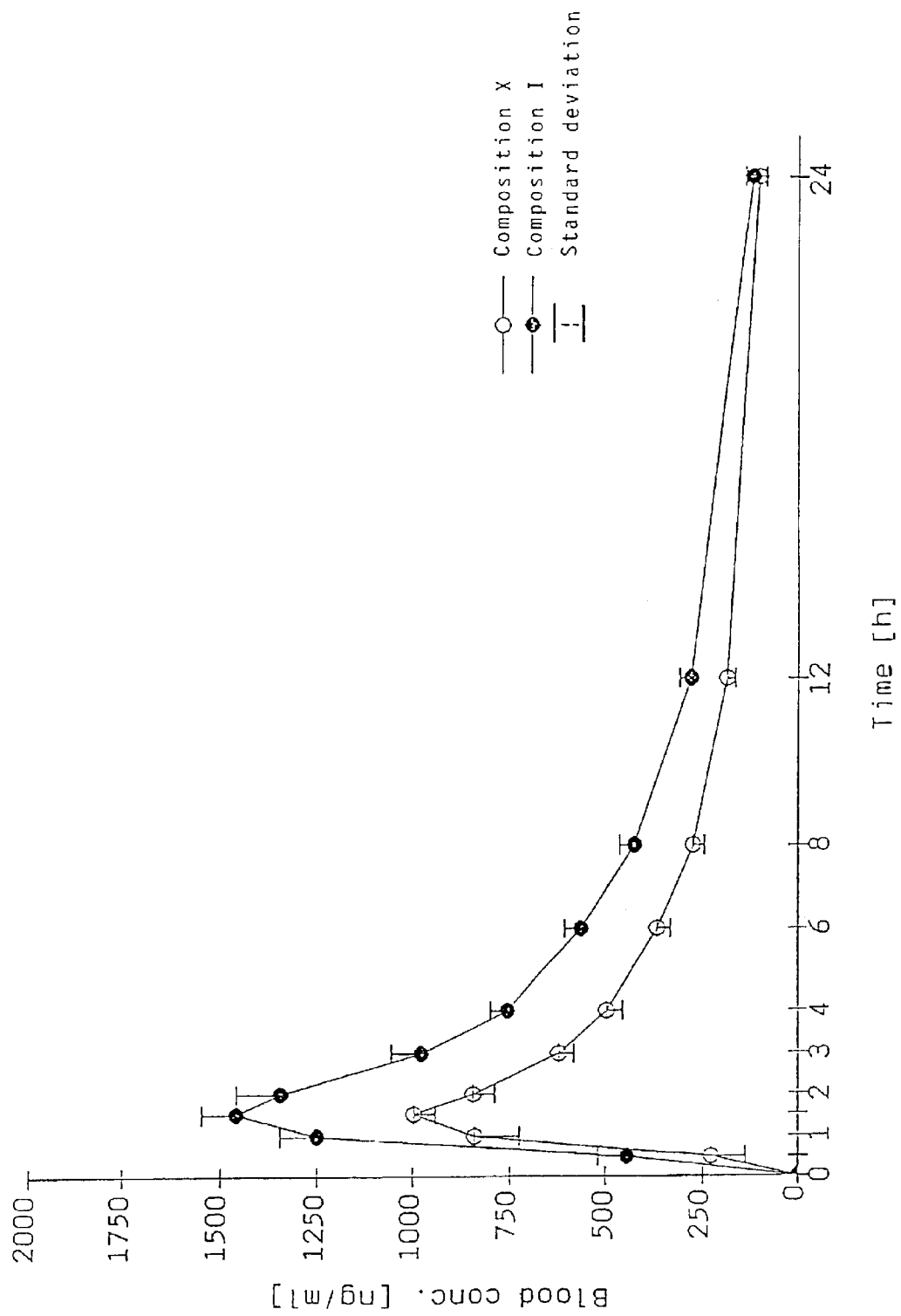
Fig. II

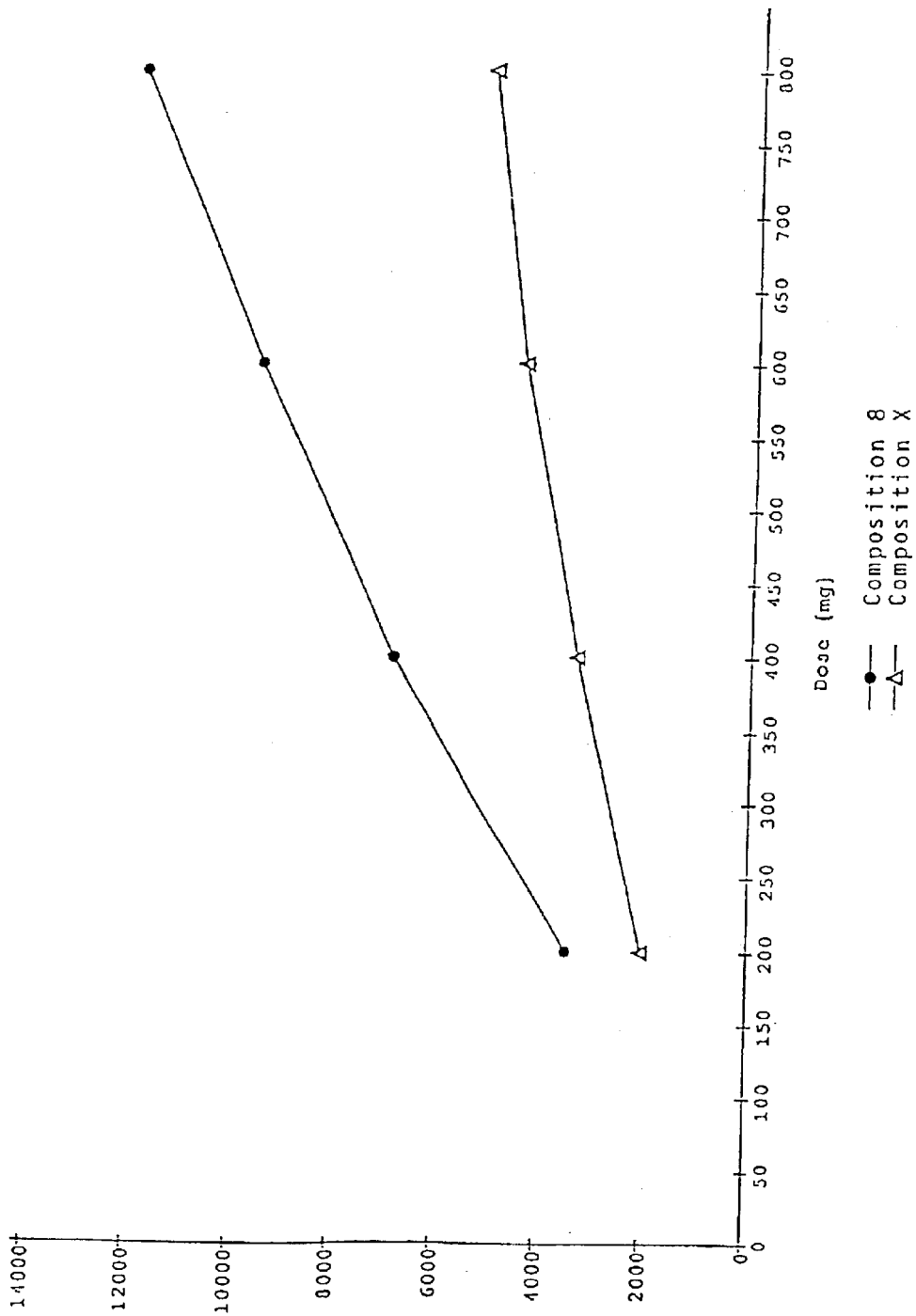

PHARMACEUTICAL COMPOSITION

This is a continuation of U.S. application Ser. No. 10/094,781 Mar. 11, 2002, abandoned; which is a continuation of U.S. application Ser. No. 09/871,858, Jun. 1, 2001, abandoned; which is a continuation of U.S. application Ser. No. 09/690,400, Oct. 17, 2000, U.S. Pat. No. 6,258,808; which is a continuation of U.S. application. Ser. No. 09/488,215, Jan. 19, 2000, U.S. Pat. No. 6,262,022; which is a continuation of U.S. application. Ser. No. 09/312,170, May 14, 1999, abandoned; which is a continuation of U.S. application Ser. No. 08/979,495, Nov. 26, 1997, abandoned; which is a continuation of U.S. application. Ser. No. 08/490,600, Jun. 6, 1995, abandoned; which is a continuation of U.S. application. Ser. No. 08/233,152, Apr. 25, 1994, abandoned; which is a continuation of U.S. application. Ser. No. 07/906,208, Jun. 25, 1992, abandoned.

PHARMACEUTICAL COMPOSITION

The present invention relates to novel galenic formulations, in particular novel galenic formulations in which the active ingredient comprises one or more members selected from cyclic poly-N-methylated undecapeptides of the cyclosporin class—see e.g. GB patent publications nos. 2 222 770 A and 2 228 198 A and equivalents world-wide.

As discussed in the said GB patent publications, the cyclosporins present highly specific difficulties in relation to administration generally and galenic formulation in particular, including in particular problems of drug bioavailability and variability in patient dose response.

In order to meet these and related difficulties, in GB patent publication no. 2 222 770 A, galenic formulations are disclosed comprising a cyclosporin as active ingredient and which take the form of, inter alia, a microemulsion or microemulsion pre-concentrate. Such compositions typically comprise 1) a hydrophilic phase, 2) a lipophilic phase and 3) a surfactant. Specifically recited hydrophilic phase components are the products known and commercially available under the trade names Transcutol and Glycofurol as well as 1,2-propylene glycol. Preferred lipophilic phase components are medium chain fatty acid triglycerides such as known and commercially available under the trade names Miglyol, Captex, Myritol, Capmul, Captex, Neobee and Mazol, Miglyol 812 being the most preferred.

Suitable surfactant components include, in particular, reaction products of natural or hydrogenated vegetable oils and ethylene glycol such as those known and commercially available under the trade names Cremophor and Nikkol, the products Cremophor RH40 and Nikkol HCO-40 being indicated as especially preferred.

GB patent publication no. 2 228 198 A proposes an alternative means for meeting difficulties in relation to cyclosporin administration. Specifically it discloses oil based formulations in which the oily component comprises a combination of tri-glyceride and (i) glycerol partial esters or (ii) 1,2-propylene glycol complete or partial esters or (iii) sorbitol complete or partial esters. The products known and commercially available under the tradename Maisine are proposed as suitable tri- and partial glyceride components. The disclosed compositions additionally comprise a surfactant component, for example Cremophor RH40, but are preferably free of any hydrophilic components such as ethanol. Described and exemplified compositions are free of such components.

In accordance with the present invention it has now surprisingly been found that particularly stable cyclosporin galenic formulations having particularly interesting bioavailability characteristics and reduced variability in inter- and intra-subject bioavailability parameters, are obtainable. Such compositions being new, the present invention provides in its broadest aspect:

A pharmaceutical composition comprising a cyclosporin as active ingredient in a carrier medium comprising:
1) 1,2-propylene glycol;
2) a mixed mono-, di-, tri-glyceride; and
3) a hydrophilic surfactant.

The term "pharmaceutical composition" as used herein and in the accompanying claims is to be understood as defining compositions of which the individual components or ingredients are themselves pharmaceutically acceptable, e.g. where oral administration is foreseen, suitable or acceptable for oral application.

Cyclosporins to which the present invention applies are any of those having pharmaceutical utility, e.g. as immunosuppressive agents, anti-parasitic agents and agents for the reversal of multi-drug resistance, as known and described in the art, in particular Cyclosporin A (also known as and referred to hereinafter as Ciclosporin), Cyclosporin G, [O-(2-hydroxyethyl)-(D)Ser]$^8$-Ciclosporin, and [3'-deshydroxy-3'-keto-MeBmt]$^1$-[Val]$^2$-Ciclosporin.

Components (2) in the compositions of the invention preferably comprise mixtures of $C_{12-20}$ fatty acid mono-, di- and tri-glycerides, especially $C_{16-18}$ fatty acid mono-, di- and triglycerides. The fatty acid component of said mixed mono-, di- and tri-glycerides may comprise both saturated and unsaturated fatty acid residues. Preferably however they will predominantly be comprised of unsaturated fatty acid residues in particular, $C_{18}$ unsaturated fatty acid residues for example linolenic, linoleic and oleic acid residues. Suitably component (2) will comprise at least 60%, preferably at least 75%, more preferably 85% or more by weight $C_{18}$ unsaturated fatty acid, e.g. linolenic, linoleic and oleic acid mono-, di- and tri-glycerides. Suitably they will comprise less than 20%, e.g. ca. 15% or 10% by weight or less, saturated fatty acid, e.g. palmitic and stearic acid mono-, di- and tri-glycerides.

Components (2) in the compositions of the invention will preferably be predominantly comprised of mono- and di-glycerides, e.g. comprise at least 50%, more preferably at least 70%, e.g. 75%, 80%, 85% by weight or more, mono- and di-glycerides, based on the total weight of component (2).

Components (2) in the compositions of the invention will suitably comprise from about 25 to about 50%, preferably from about 30 to about 40%, e.g. 35 to 40%, monoglycerides, based on the total weight of component (2).

Components (2) in the composition of the invention will suitably comprise from about 30 to about 60%, preferably from about 40 to about 55%, e.g. about 48 to 50%, di-glycerides, based on the total weight of component (2).

Components (2) in the compositions of the invention will suitably comprise at least 5%, e.g. from about 7.5 to about 15%, e.g. 9 to 12%, by weight of triglycerides.

Components (2) in the compositions of the invention may be prepared by admixture of individual mono-, di- or tri-glycerides in appropriate relative proportion. Conveniently however they will comprise transesterification products of vegetable oils, for example almond oil, ground nut oil, olive oil, peach oil, palm oil or, preferably, corn oil, sunflower oil or safflower oil and most preferably corn oil, with glycerol.

Such transesterification products are generally obtained by heating of the selected vegetable oil with glycerol, at high temperature in the presence of an appropriate catalyst under an inert atmosphere with continuous agitation, e.g. in a stainless steel reactor, to effect trans-esterification or glycerolysis. In addition to their mono-, di- and tri-glyceride components, such transestrification products will also generally comprise minor amounts of free glycerol. The amount of free glycerol present in components (2) for use in the compositions of the invention will preferably be less than 10%, more preferably less than 5%, most preferably ca. 1 or 2% by weight based on the total weight of free glycerol plus mono-, di- and tri-glycerides.

Preferably some of the glycerol is first removed e.g. by distillation (to give a "substantially glycerol free batch"), when soft gelatine capsules are to be made.

Especially suitable components (2) for use in the compositions of the invention will thus comprise the following components in the indicated amounts by weight based on the total weight of component (2):

Mono-glycerides: 25 or 30 to 50%, especially 30 to 40%. Di-glycerides: 30 or 40 to 60%, especially 40 to 55%, e.g. 45 to 55%. Mono- plus di-glycerides: >75%, especially >80%, e.g. ca. 85%. Tri-glycerides: at least 5%. Free glycerol: <5%, preferably <2% or <1%.

Particularly suitable components (2) for use in the compositions of the invention are trans-esterification products of corn oil and glycerol, for example as commercially available under the trade name Maisine. Such products are comprised predominantly of linoleic and oleic acid mono-, di- and tri-glycerides together with minor amounts of palmitic and stearic acid mono-, di- and tri-glycerides (corn oil itself being comprised of ca. 56% by weight linoleic acid, 30% oleic acid, ca. 10% palmitic and ca. 3% stearic acid constituents). Physical characteristics for Maisine [available from the company Etablissements Gattefossé, of 36, Chemin de Genas, P.O.Box 603, 69804 Saint-Priest, Cedex (France)] are: approximate composition

| | |
|---|---|
| free glycerol | 10% max. (typically 3.9–4.9% or, in "substantially glycerol free" batches, ca. 0.2%) |
| mono-glycerides | ca. 35% (typically 30–40% or, in "substantially glycerol free" batches, e.g. 32–36, e.g. ca. 36%) |
| di-glycerides | ca. 50% (or, in "substantially glycerol free" batches ca. 46–48%) |
| tri-glycerides | ca. 10% (or, in "substantially glycerol free" batches, ca. 12–15%) |
| free oleic acid content | ca. 1% |

Further physical characteristics for Maisine are: acid value=max. ca. 2, iodine no.=ca. 85–105, saponification no.=ca. 150–175 (Fiedler "Lexikon der Hilfsstoffe", 3rd revised and expanded edition (1989) Vol. 2, p.768). The fatty acid content for Maisine is typically: palmitic acid—ca. 11%; stearic acid—ca. 2.5%; oleic acid—ca. 29%; linoleic acid—ca. 56%; others—ca. 1.5%.

It is especially preferred that the component (2) e.g. a glycerol transesterified corn oil is clear, e.g. after keeping a sample in a refrigerator, e.g. between 2 and 8° C., for 24 hours, the sample is clear at room temperature 1 hour after taking the sample out of the refrigerator.

Preferably components (2) have a low saturated fatty acid content. Components (2) meeting these requirements may, for example be obtained from commercially available products, e.g. obtained therefrom by methods such as separative techniques as known in the art, e.g. freezing procedures coupled with separative techniques, e.g. centrifugation, to remove the saturated fatty acid components/enhance the unsaturated fatty acid component content. Typically the total saturated fatty acid component content will be <15%, e.g. <10%, or <5% by weight based on the total weight of component (2). A reduction of the content of saturated fatty acid component in the mono-glyceride fraction of components (2) may be observed after the separative technique.

Components (2) thus preferably contain lesser quantities of saturated fatty acids (e.g. palmitic and stearic acids) and relatively greater quantities of unsaturated fatty acids (e.g. oleic and linoleic acids) than for the starting material.

Typical preferred components (2) may according to the preferred embodiment of this invention contain:

| | |
|---|---|
| 32–36% | mono-glycerides, |
| 45–55% | di-glycerides and |
| 12-20% | tri-glycerides | by weight based on the total weight of component (2).

Further preferred characteristics include the following:

Fatty acid content as determined as the methyl ester by chromatography

| | |
|---|---|
| Methyl linoleate | 53–63% |
| Methyl oleate | 24–34% |
| Methyl linolenate | 0–3% |
| Methyl arachate | 0–3% |
| Methyl palmitate | 6–12% |
| Methyl stearate | 1–3% |
| Relative Density | 0.94–0.96 |
| Hydroxyl Value | 140–210 |
| Iodine Value | 110–120 |
| Peroxide Value | <4.0 |
| Free Glycerol | <1.0 |
| Acid value max. | ca. 2 |
| Saponification no. ca. | 150–185 |

Components (2) complying with the above outlined features are referred to hereafter as "refined glycerol-transesterified corn oils". Freshly prepared components (2) according to the preferred embodiments are of clear appearance and stay clear at storage temperature of 20° C.–25° C. for more than 20 days.

The "refined glycerol-transesterified corn oils" have especially been proposed for the preparation of the compositions of this invention. They may also have uses for the solubilization of other active agents and have the advantage of remaining stable, e.g. clear, for a long time. They constitute another aspect of present invention. The invention accordingly provides in another aspect a trans-esterification product of corn oil and glycerol comprising predominately of linoleic acid and oleic acid mono-, di- and tri-glycerides treated to enhance the unsaturated fatty acid component content of mono-, di- and tri-glycerides so that the linoleic acid and oleic acid mono-, di- and tri-glyceride content is in total 85% or more of the whole composition.

Components (3) in the compositions of the invention preferably have an HLB of at least 10.

Examples of suitable components (3) in the compositions of the invention are:

3.1 Reaction products of a natural or hydrogenated castor oil and ethylene oxide. Such products may be obtained in known manner, e.g. by reaction of a natural or hydrogenated castor oil with ethylene oxide, e.g. in a molar ratio of from about 1:35 to about 1:60, with optional removal of the polyethyleneglycol component from the product, e.g. in accordance with the methods disclosed in German Auslegeschriften 1,182,388 and 1,518,819. Especially suitable are the various tensides available under the trade name Cremophor. Particularly suitable are the products Cremophor RH 40 having a saponification number of ca. 50–60, an acid number <1, an iodine number <1, a water content (Fischer) <2%, an $n_D^{60}$ of ca. 1,453–1,457 and an HLB of ca. 14–16; Cremophor RH 60 having a saponification number of ca. 40–50, an acid number <1, an iodine number <1, a water content (Fischer) 4.5–5.5%, and an $n_D^{25}$ of ca. 1.453–1.457 and an HLB of ca. 15–17; and Cremophor EL having a molecular weight (by steam osmometry) of ca. 1630, a saponification number of ca. 65–70, an acid number of ca. 2, an iodine number of ca. 28–32 and an $n_D^{25}$ of ca. 1.471.(c.f. Fiedler, "lexikon der Hilfstoffe", 3rd revised and expanded edition (1989), Vol. 1, p. 326). Also suitable for use in this category are the various tensides available under the trade name Nikkol (e.g. Nikkol HCO-40 and HCO-60), Emulgin (e.g. Emulgin RO40), Mapeg (e.g. Mapeg CO-40h) and Incrocas (e.g. Incrocas 40) (c.f. Fiedler). The said product Nikkol HCO-60 is a reaction product of hydrogenated castor oil and ethylene oxide exhibiting the following characteristics: acid value ca. 0.3; saponification number of ca. 47.4; hydroxy value of ca. 42.5; pH (5%) of ca. 4.6; color APHA=ca. 40; m.p.=ca. 36.0° C.; freezing point=ca. 32.4° C.; $H_2O$ content (%, KF)= 0.03.

3.2 Polyoxyethylene-sorbitan-fatty acid esters, e.g. mono- and tri-lauryl, palmityl, stearyl and oleyl esters, e.g. of the type known and commercially available under the trade name Tween (c.f. Fiedler, loc.cit. p.1300–1304) including the products Tween
   20 [polyoxyethylene(20)sorbitanmonolaurate],
   21 [polyoxyethylene(4)sorbitanmonolaurate],
   40 [polyoxyethylene(20)sorbitanmonopalmitate],
   60 [polyoxyethylene(20)sorbitanmonostearate],
   65 [polyoxyethylene(20)sorbitantristearate],
   80 [polyoxyethylene(20)sorbitanmonooleate],
   81 [polyoxyethylene(5)sorbitanmonooleate],
   85 [polyoxyethylene(20)sorbitantrioleate].

Especially preferred products of this class for use in the compositions of the invention are the above products Tween 40 and Tween 80.

3.3 Polyoxyethylene fatty acid esters, for example polyoxyethylene stearic acid esters of the type known and commercially available under the trade name Myrj (c.f. Fiedler, loc. cit., 2, p.834–835); an especially preferred product of this class for use in the compositions of the invention is the product Myrj 52 having a $D^{25}$=ca. 1.1., m.p.=ca. 40–44° C., an HLB value=ca. 16.9., an acid value=ca. 0–1 and a saponification no.=ca. 25–35.

3.4 Polyoxyethylene-polyoxypropylene co-polymers and block co-polymers, e.g. of the type known and commercially available under the trade names Pluronic, Emkalyx and Poloxamer (c.f. Fiedler, loc. cit., 2, p. 959). An especially preferred product of this class for use in the compositions of the invention is the product Pluronic F68, having an m.p.=ca. 52° C. and a molecular weight of ca. 6800–8975. A further preferred product of this class for use in the compositions of the invention is the product Poloxamer 188.

3.5 Dioctylsulfosuccinate or di-[2-ethylhexyl]-succinate (c.f. Fiedler, loc. cit., 1, p. 107–108).

3.6 Phospholipids, in particular lecithins (c.f. Fiedler, loc. cit., 2, p. 943–944). Lecithins suitable for use in the compositions of the invention include, in particular, soya bean lecithins.

3.7 Propylene glycol mono- and di-fatty acid esters such as propylene glycol dicaprylate (also known and commercially available under the trade name Miglyol 840), propylene glycol dilaurate, propylene glycol hydroxystearate, propylene glycol isostearate, propylene glycol laurate, propylene glycol ricinoleate, propylene glycol stearate and so forth (c.f. Fiedler, loc. cit., 2, p. 808–809).

3.8 Sodium lauryl sulfate.

For use in relation to the present invention, components as set out under (3.1) above are most preferred.

Components (1), (2) and (3) are preferably present in the compositions of the invention in relative proportions such that the composition is a "micro-emulsion preconcentrate", i.e. having the characteristics of a micro-emulsion preconcentrate system as described in GB patent publication no. 2 222 770 A at pages 11 to 12, the contents of which are, for the purposes of defining such systems, incorporated herein by reference. Compositions of the invention are thus preferably "microemulsion preconcentrates", in particular of the type providing o/w (oil-in-water) microemulsions. The present invention is also to be understood as including compositions comprising components (1), (2) and (3) together with (4) water and which are microemulsions.

As also indicated in GB patent publication no. 2 222 770 A the hydrophilic phase of microemulsion preconcentrate systems, i.e. component (1) in compositions of the present invention may include one or more additional ingredients as hydrophilic phase component, for example lower (e.g. $C_{1-5}$) alkanols, in particular ethanol. Such components will generally be present in partial replacement of component (1). While the use of ethanol in compositions of the present invention is not essential, it has been found to be of particular advantage when the compositions are to be manufactured in soft gelatine encapsulated form, e.g. as a means of improving storage characteristics, in particular to reduce risk of cyclosporin precipitation following encapsulation procedures. Thus the shelf life stability may be extended by employing a lower alkanol as an additional ingredient of the hydrophilic phase.

Suitably the hydrophilic phase component, i.e. component (1), 1,2-propylene glycol, or component (1) plus any hydrophilic phase co-component(s), e.g. ethanol, will be present in the compositions of the invention in an amount of from 1.0 or 2.5 to 50%, preferably from 5 to 40%, more preferably from 10 to 35%, e.g. above 15%, e.g. from about 20 to about 30% by weight based on the total weight of hydrophilic phase component(s) plus components (2) and (3).

When a hydrophilic phase co-component is employed, the co-component, e.g. ethanol, is suitably present in an amount of up to about 20%, preferably up to about 10 or 15%, e.g. from about 5 to 10 or 15% by weight based in the total weight of the composition. Such co-component is thus suitably present in an amount of from about 25 to 75% by weight based on the total weight of hydrophilic phase components (e.g. 1,2-propylene glycol plus ethanol) more preferably it is present in an amount of less than 50%, e.g. from 25 to 50%, for example about 30, 40 or 50%.

Suitably component (2) will be present in the compositions of the invention in an amount of from 5 to 65%, preferably from 15 to 45%, more preferably from 20 to 40%, e.g. from about 25 to about 35%, based on the total weight of hydrophilic phase component(s) plus components component (2) and component (3).

Suitably component (3) will be present in the compositions of the invention in an amount of from 25 to 75%, preferably from 30 to 60%, e.g. from about 55 or 60% based on the total weight of hydrophilic phase component(s) plus components (2) and component (3).

Suitably the compositions of the invention will comprise from about 1 or 2 to 30%, preferably from 5 to 20 or 25%, more preferably from 7.5 to 15%, e.g. about 10% by weight of cyclosporin based on the total weight of the composition.

Accompanying FIG. 1 represents a three-way plot for relative concentrations of hydrophilic phase component, i.e. 1,2-propylene glycol, component (2), e.g. "refined glycerol-transesterified corn oil", and component (3), e.g. Cremophor RH40, in compositions in accordance with the invention and comprising 10% cyclosporin (e.g. Ciclosporin) by weight. Relative concentrations of the carrier components increase in the directions indicated by the arrows from 0 to 100%.

For compositions in accordance with the present invention the relative proportion of hydrophilic phase component (s), component (2) and component (3) will suitably lie within the shaded area X. Compositions thus defined are microemulsion preconcentrates of high stability, capable on addition to water, of providing microemulsions having an average particle size of <1,500 Å and stable over periods in excess of 24 hrs. In contrast compositions in the region A, B and C give aqueous systems subject to (A) discoloration, (B) phase separation and (C) turbidity respectively. Compositions in accordance with the invention comprising hydrophilic phase component(s) and components (2) and component (3) in relative proportion as defined by the line X of FIG. 1 are accordingly especially preferred.

In the event that the 1,2-propylene glycol component is partially replaced by ethanol as hereinbefore described, the area X of FIG. 1 is shifted slightly upwards within the plot, i.e. in the direction of higher component (3) concentration. This shift however represents an upwards displacement of a few percent only and does not substantially alter the obtained plot.

The compositions of the invention show good stability characteristics, e.g. as indicated by standard stability trials, e.g. having a shelf life stability of up to three years, and even longer.

Compositions in accordance with the present invention may also include further additives or ingredients, for example [e.g. antioxidants ascorbyl palmitate, butyl hydroxy anisole (BHA), butyl hydroxy toluene (BHT) and tocopherols, e.g. α-tocopherol (vitamin E)] and/or preserving agents, e.g. in an amount of from about 0.05 to 1% by weight based on the total weight of the composition, or sweetening or flavoring agents, e.g. in an amount of up to about 2.5 or 5% by weight based on the total weight of the composition.

Compositions in accordance with the present invention have been found to exhibit especially advantageous properties when administered orally, e.g. in terms of both the consistency and high level of bioavailability achieved as indicated in standard bioavailability trials e.g. in healthy patients using a specific monoclonal kit to determine cyclosporin levels, e.g. as described in the Examples hereinafter. In particular the compositions in accordance with the present invention provide an improved oral administration form for cyclosporins (e.g. Ciclosporin) as it exhibits absence of significant food interaction, which we have observed with the commercially available oral form of Ciclosporin especially with fat rich food. Moreover, inter-subject and intra-subject variability of pharmacokinetic parameters may be significantly lower with the compositions according to the present invention than with the commercial oral form of Ciclosporin. Specifically the difference between the pharmacokinetic parameters with food intake and without food intake, or even between day time absorption and night time absorption, may be eliminated by administering the composition in accordance with the present invention. Thus with the novel composition according to present invention the pharmacokinetic parameters, e.g. absorption and blood levels, become surprisingly more predictable and this new galenic form may eliminate problems in administration with erratic absorption of Ciclosporin. Additionally the composition according to present invention, may exhibit an improved bioavailability in patients having malabsorption, e.g. liver transplantation patients or pediatric patients. In particular it has been found that such compositions are compatible with tenside materials, e.g bile salts, present in the gastro-intestinal tract. That is, they are fully dispersible in aqueous systems comprising such natural tensides and are thus capable of providing micro-emulsion systems in situ which are stable and do not exhibit precipitation of the cyclosporin or other disruption of fine particulate structure. Function of such systems on oral administration remains independent of and/or unimpaired by the relative presence or absence of bile salts at any particular time or for any given individual.

The compositions of the invention are well tolerated, e.g. as indicated by clinical trials over 4 weeks.

Compositions in accordance with the present invention will preferably be compounded in unit dosage form, e.g. by filling into orally administerable capsule shells, e.g. soft or hard gelatine capsule shells but if desired may be in drink solution form. Where compositions are in unit dosage form, each unit dosage will suitably contain between 10 and 200 mg cyclosporin, more suitably between 10 and 150 mg, e.g. 15, 20, 25, 50 or 100 mg cyclosporin. Such unit dosage forms are suitable for administration 1×, 2× or 3× up to 5× daily (e.g. depending on the particular purpose of therapy, the phase of therapy etc.).

The compositions of the invention containing Ciclosporin are indicated to be administered at the same dosage for renal transplant patients as the commercial forms as described hereafter.

Alternatively compositions in accordance with the present invention suitable for oral administration may include (4) water or any other aqueous system, to provide microemulsion systems suitable for drinking.

In addition to the foregoing the present invention also provides a process for the production of a pharmaceutical composition as hereinbefore defined, which process comprises bringing a component (1), a component (2) and a component (3) as hereinbefore defined into intimate admixture and, when required compounding the obtained composition in unit dosage form, for example filing said composition into gelatine, e.g. soft or hard gelatine, capsules.

In a more particular embodiment the present invention provides a process for the production of a pharmaceutical composition as hereinbefore defined in the form of a "microemulsion preconcentrate" or microemulsion, which method comprises bringing a component (1), a component (2) and a component (3), optionally together with further components or additives, in particular with a hydrophilic phase co-component, for example ethanol, into intimate admixture in relative proportions of components component (1), component (2) and component (3), such that a micro-emulsion preconcentrate is obtained and, when required, compounding the obtained composition in unit dosage form or combining said obtained composition with sufficient water or sufficient of an aqueous solvent medium such that a microemulsion is obtained.

The following examples are illustrative of compositions in accordance with the invention, in unit dosage form, suitable for use, e.g. in the prevention of transplant rejection or for the treatment of autoimmune disease, on administration of from 1 to 5 unit dosages/day. The examples are described with particular reference to Ciclosporin. However equivalent compositions may be obtained employing any other cyclosporin, in particular [0-(2-hydroxyethyl)-(D)-Ser]$^8$-Ciclosporin (hereinafter referred to as Compound Z).

EXAMPLE 1

Preparation of "refined glycerol-transesterified corn oil".

Substantially-glycerol free glycerol-transesterified corn oil (if necessary after heating to give a clear mixture) is slowly cooled to a temperature of +20° C. and kept at this temperature for one night. In a first-step centrifugation, at an acceleration of 12 000 G and a flow rate of 103 kg/h in a continuous flow centrifuge, a liquid phase (62 kg/h) and a sediment-containing phase (41 kg/h) are obtained. The liquid phase is slowly cooled to +8° C. and kept at this temperature for one night. In a second-step centrifugation at an acceleration of 12 000 G and a flow rate of 112 kg/h a liquid phase (76.2 kg/h) and a sediment-containing phase (35.8 kg/h) are obtained. The liquid phase is "refined glycerol-transesterified corn oil". Alternatively an improved product may be obtained by effecting the centrifugation in three steps, e.g. at +20° C., +10° C. and +5° C.

The process is characterised by a slight percentage reduction in the mono-glyceride component in the refined glycerol transesterified corn oil as compared to the starting material (e.g. 35.6% compared to 38.3%).

A typical analytical comparison between the sediment and clear solution is as follows:

| Compound | Sediment (%) | Clear Solution (%) |
| --- | --- | --- |
| 1. Mono palmitate | 19.1 | 3.4 |
| 2. Mono linoleate + Mono oleate | 23.4 | 27.0 |
| 3. Mono stearate | 5.7 | <2 |
| 4. Dilinoleate + Dioleate | 35.4 | 44.7 |
| 5. Other di-glycerides | 7.7 | 10.4 |
| 6. Tri-glycerides | 8.7 | 12.5 |

In a variant of this refining procedure similar "refined glycerol-transesterified corn oil" compositions may be obtained by heating the starting material to +80° C. for one hour under nitrogen, cooling it down with slight agitation and with a 1° C. difference between temperature of the product and temperature of the cooling fluid to +16° C., maintaining +16° C. for about 12 hours with slight agitation, cooling it down to about +8° C. and separating the precipitate by means of a band filter under vacuum.

In a further variant similar "refined glycerol-transesterified corn oil" compositions may be obtained by heating the starting material to +75° C. under nitrogen and cooling it down to +8° C. within a period of 5 to 6 hours.

In yet a further variant similar "refined glycerol-transesterified corn oil" compositions may be obtained by heating the starting material to +80° C. for 1 hour, cooling it down to +8° C. in a stepwise cooling procedure comprising: cooling to +25° C. in 1 hour, maintaining at +25° C. for 8 hours, cooling to +20° C. in 0.5 hours, maintaining at +20° C. for 1 hour, cooling to +15° C. in 0.5 hours, maintaining at +15° C. for 1 hour, cooling to +10° C. in 0.5 hours, maintaining at +10° C. for 1 hour, cooling to +8° C. in 0.5 hours, staying at 8° C. for 2 hours, and filtering the batch on a 0.5 μm mesh filter under a pressure of 0.5 bars.

Typical contents of components in the refined product obtained from these preparations are listed in the following Table:

| COMPOSITION OF COMPONENTS (% w/w) | |
| --- | --- |
| Components | refined glycerol-transesterified corn oil |
| Glycerides: mono | 33.3 |
| di | 52.1 |
| tri | 14.6 |
| Fatty acids: | |
| palmitic acid (C16) | 7.8 |
| stearic acid (C18) | 1.7 |
| oleic acid (C18:1) | 31.6 |
| linoleic acid (C18:2) | 57.7 |
| Glycerol content | <1% |

EXAMPLE 2

Preparation of oral unit dosage forms

| COMPONENT | QUANTITY (mg/capsule) |
| --- | --- |
| Cyclosporin, e.g. Ciclosporin | 100 |
| 1) 1,2-propylene glycol | 200 |
| 2) refined oil | 320 |
| 3) Cremophor RH40 | 380 |
| Total | 1,000 |

The cyclosporin is dissolved in component (1) with stirring at room temperature and (2) and (3) are added to the obtained solution again with stirring. The obtained mixture is filled into size 1 hard gelatine capsules and sealed e.g. using the Quali-Seal technique.

Compositions comprising 50 and 100 mg Ciclosporin, are prepared analogously employing the following indicated ingredients in the indicated amounts.

In this Example, refined oil="refined glycerol-transesterified corn oil" as described in Example 1 or Maisine, e.g. substantially glycerol free Maisine.

COMPOSITIONS COMPRISING 100 mg cyclosporin, e.g. Ciclosporin

| | COMPOSITION | | | | |
| --- | --- | --- | --- | --- | --- |
| | 2 | 3 | 4 | 5 | 6 |
| COMPONENT | QUANTITY (mg/capsule) | | | | |
| 1) 1,2-Propylene glycol | 200 | 270 | 180 | 180 | 90 |
| 2) refined oil | 350 | 180 | 180 | 360 | 360 |
| 3) Cremophor RH40 | 350 | 450 | 540 | 360 | 450 |

-continued

COMPOSITIONS COMPRISING 100 mg cyclosporin, e.g. Ciclosporin

| COMPONENT | COMPOSITION | | | |
|---|---|---|---|---|
| | 7 | 8 | 9 | 10 |
| | QUANTITY (mg/capsule) | | | |
| 1) 1,2-Propylene glycol | 150 | 100 | 200 | 200 |
| 1a) ethanol | 100 | 100 | 100 | 100 |
| 2) refined oil | 345 | 320 | 320 | 290 |
| 3) Cremophor RH40 | 405 | 380 | 380 | 360 |

COMPOSITIONS COMPRISING 50 mg Ciclosporin

| COMPONENT | COMPOSITION | | | | | |
|---|---|---|---|---|---|---|
| | A | B | C | D | E | F |
| | QUANTITY (mg/capsule) | | | | | |
| 1) 1,2-Propylene glycol | 100 | 135 | 45 | 90 | 100 | 50 |
| 1a) ethanol | | | | | | 50 |
| 2) refined oil | 160 | 90 | 180 | 180 | 67 | 160 |
| 3) Cremophor RH40 | 190 | 225 | 225 | 180 | 167 | 190 |

As indicated above equivalent compositions may be made containing Compound Z instead of Ciclosporin. Thus composition D may be made containing 50 mg Compound Z instead of Ciclosporin.

EXAMPLE 3
Bioavailability in Dogs

The biopharmaceutical properties of compositions in accordance with the present invention we compared with the marketed soft-gelatine capsule of Ciclosporin. The forms were compared after oral administration to 12 male beagle dogs in a cross-over design. The pharmacokinetic profile of Ciclosporin was determined in whole blood over 24 hours. the areas under the curve of the blood concentration versus time curves (AUC), $C_{max}$ and $T_{max}$ were determined.

Forms: Dose 100 mg Ciclosporin/dog

| Composition X (commercial form, soft gelatin capsule) | |
|---|---|
| Ciclosporin | 100 mg |
| Labrafil | 300 mg |
| ethanol | 100 mg |
| Maize oil | 416 mg |
| Total | 926 mg/dosage |
| Composition I according to present invention (a soft gelatin capsule): | |
| Ciclosporin | 100 mg |
| 1) 1,2-propylene glycol | 75 mg |
| 1a) ethanol | 150 mg |
| 2) refined glycerol-transesterified corn oil | 345 mg |
| 3) Cremophor RH40 | 405 mg |
| Total | 1075 mg/dosage |

Drug Administration 10 male beagle dogs weighing around 12 kg completed the trial successfully. Twenty hours before the drug administration the food was withdrawn but the animals were allowed free access to water until the beginning of the experiment. The dosage forms were administered by gavage to the animals, early in the morning (approx. 8.00 am), and followed by 20 ml NaCl 0.9% solution. Three hours after the administration, the animals were again allowed free access to water and food. A 1 week wash-out period was necessary between 2 administrations to the same animal.

Blood Sampling

Blood samples of 2 ml (or 5 ml for the blank sample) were taken from the vena cephalica (forearm) with a sterile needle (diameter ca. 1.2 mm) and collected into 5 ml plastic tubes containing EDTA at −15 min, 30 min, 1, 1.5, 2, 3, 4, 6, 8, 12 and 24 hours after the oral administration of the drug. The blood samples were stored at ca. −18° C. until drug assay. The blood samples were analysed by Ciclosporin-specific radioimmunoassay (RIA). The median blood concentrations of Ciclosporin in dogs are plotted in the accompanying FIG. 2 The areas under the blood drug concentration versus time curves (AUC) were calculated using the trapezoidal rule. An analysis (CV) of variance was performed and the mean AUCs, Cmax and Tmax were compared statistically by the Tukey test. The results obtained are shown in the following table.

| | $AUC_{0-24 h}$ | | $C_{max}$ | | $T_{max}$ | |
|---|---|---|---|---|---|---|
| Composition | Mean [ng · h/ml] | CV [%] | Mean [ng/ml] | CV [%] | Mean [h] | CV [%] |
| X | 6695 | 27 | 1053 | 25 | 1.3 | 20 |
| I | 10064 | 24 | 1539 | 18 | 1.6 | 29 |

The behaviour and body weight of the animals were controlled during the study. No body weight loss could be detected.

Conclusion: The composition according to the present invention (composition I) has a significantly higher bioavailability (factor 1.5) than the commercial soft-gelatin capsule of Ciclosporin.

FIG. 2 shows the average whole blood Ciclosporin concentrations as determined by a specific monoclonal RIA following single oral administration of Composition X and Composition I each in 100 mg dosage. Blood concentration (in ng/ml) is recorded vertically and time horizontally.

EXAMPLE 4
Bioavailability in Humans

The bioavailability of Ciclosporin is compared as it is determinable after administration of the commercial Ciclosporin soft gelatine capsule and of a composition according to present invention.

Administered form: 100 mg Ciclosporin per capsule

| Composition X (commercial form, soft gelatine capsule) | |
|---|---|
| Ciclosporin | 100 mg |
| Labrafil | 300 mg |
| Ethanol | 100 mg |
| Maize oil | 426 mg |
| Total | 926 mg/Capsule |

Composition No. 8 (according to Example 2 containing "refined glycerol-transesterified corn oil") in a soft gelatine capsule.

Method:

Forty eight healthy male subjects completed the study. Each of the participants received four of the eight administrations (two doses of composition 8 and the same two doses of composition X).

The participants were randomly allocated to two subgroups consisting of twenty four subjects each according to a parallel design. Subjects in Group I received doses of 200 mg and 600 mg Ciclosporin and subjects in Group II received 400 mg and 800 mg.

Within each of the two groups the trial was conducted on the basis of a balanced 4-way cross-over design with a wash-out period of two weeks between each treatment.

Blood samples for determination of Ciclosporin in whole blood were taken 1 minute before drug intake and then 15 min, 30 min. 45 min, 1 h, 1.5h, 2 h, 2.5 h, 3 h, 3.5 h, 4 h, 4.5 h, 5 h, 6 h, 8 h, 20 h, 12 h, 16 h, 20 h, 24 h, 28 h, 32 h, 36 h, 40 h, and 48 h after drug intake.

The individual concentrations of Ciclosporin in whole blood were determined for each blood sample by a specific RIA-method.

The limit of quantification was 12.5 ng/ml.

Blood concentrations and corresponding $AUC_{(0-48\ h)}$-values of Ciclosporin were significantly higher after administration of Composition 8 than after administration of Composition X at all dosage strengths. Peak concentrations ($C_{max}$) of the 200 mg, 400 mg, and 600 mg dose levels appeared somewhat earlier after administration of Composition 8 (see following table).

TABLE

Bioavailability of Ciclosporin in Humans
Mean (±SD) values of $AUC_{(0-48\ h)}$, $C_{max}$ and $T_{max}$ after single oral administration of different dosages of Composition X and Composition 8

| Form | $AUC_{(0-48\ h)}$ [ng · h/ml] | $C_{max}$ [ng/ml] | $T_{max}$ [h] |
|---|---|---|---|
| 200 mg Comp X | 2028 ± 608 | 558 ± 228 | 2.1 ± 0.7 |
| 200 mg Comp 8 | 3468 ± 1000 | 1025 ± 218 | 1.5 ± 0.4 |
| 400 mg Comp X | 3326 ± 1115 | 785 ± 252 | 2.1 ± 0.9 |
| 400 mg Comp 8 | 6944 ± 1468 | 1557 ± 286 | 1.4 ± 0.4 |
| 600 mg Comp X | 4501 ± 1217 | 917 ± 236 | 2.3 ± 1.0 |
| 600 mg Comp 8 | 9689 ± 2282 | 1812 ± 400 | 1.7 ± 0.6 |
| 800 mg Comp X | 5209 ± 1554 | 1045 ± 264 | 2.4 ± 1.0 |
| 800 mg Comp 8 | 12162 ± 3059 | 2143 ± 576 | 2.1 ± 0.8 |

Based on the mean ratios of $AUC_{(0-48\ h)}$-values the relative bioavailability of Composition 8 vs Composition X was estimated between 170% and 233%, depending on the dose administered (see following table).

TABLE

Relative bioavailability of Composition 8 vs. Composition X

| Dose of [mg] | Mean ratio of $AUC_{(0-48\ h)}$ Comp 8 vs. Comp X | Conversion Factor: Comp X vs. Comp 8 |
|---|---|---|
| 200 | 1.70 | 0.59 |
| 400 | 2.09 | 0.48 |
| 600 | 2.15 | 0.47 |
| 800 | 2.33 | 0.43 |

Conclusion: The composition according to the present invention (Composition 8) has a significantly higher bioavailability in humans be at least factor 1.7 when compared to the commercial form (Composition X).

The accompanying FIG. 3 provides a graphical plot of the mean $AUC_{(0-48\ h)}$-values of composition X (open triangles) versus those of Composition 8 (solid Circles). AUC-values (in ng.h/ml) of Ciclosporin vertically and dose horizontally as obtained from Example 4.

The extent of absorption of Composition 8 (in terms of $AUC_{(0-48\ h)}$-values) seemed to be independent of dose, whereas the extent of absorption of Composition X declined with increasing doses (see FIG. 3).

What is claimed is:

1. A trans-esterification product of corn oil and glycerol comprising
   a) a free glycerol content of less than 10%,
   b) less than 1% of palmitic acid and stearic acid mono-, di- and tri-glycerides; and
   c) 85% or more of linoleic acid and oleic acid mono-, di- and tri-glycerides all parts by weight of the whole composition.

2. A product of claim 1 having 30% to 40% by weight of mono-glycerides.

3. A product of claim 1 having 45% to 55% by weight of di-glycerides.

4. A product of claim 2 having 45% to 55% by weight of di-glycerides.

5. A product of claim 1 having from about 7.5 to about 15% by weight of tri-glycerides.

6. A product of claim 2 having from about 7.5 to about 15% by weight of tri-glycerides.

7. A product of claim 1 having a free glycerol content of less than 5% by weight.

8. A product of claim 2 having a free glycerol content of less than 5% by weight.

9. A product of claim 1 having a free glycerol content of less then 2% by weight.

10. A product of claim 2 having a free glycerol content of less than 2% by weight.

11. A product of claim 1 comprising from about 25% to about 50% by weight of mono-glycerides, from about 30% to about 60% by weight of di-glycerides, and at least 5% by weight of tri-glycerides.

12. A product of claim 11 having 30% to 40% by weight of mono-glycerides.

13. A product of claim 11 having 45% to 55% by weight of di-glycerides.

14. A product of claim 12 having 45% to 55% by weight of di-glycerides.

15. A product of claim 11 having from about 7.5 to about 15% by weight of tri-glycerides.

16. A product of claim 12 having from about 7.5 to about 15% by weight of tri-glycerides.

17. A product of claim 11 having a free glycerol content of less than 5% by weight.

18. A product of claim 11 having a free glycerol content of less than 2% by weight.

19. A pharmaceutical composition comprising an effective amount of a pharmaceutically active compound and a trans-esterification corn oil product of claim 1.

20. A method which comprises solubilizing a pharmaceutically active ingredient in a trans-esterification corn oil product of claim 1.

* * * * *